US00RE48674E

(19) United States
(12) Reissued Patent
Pastorio et al.

(10) Patent Number: US RE48,674 E
(45) Date of Reissued Patent: Aug. 10, 2021

(54) METHOD FOR THE SYNTHESIS OF 5-AMINO-1-PHENYL-3-CYANO-4-TRIFLUOROMETHYL SULFINYL

(71) Applicants: Andrea Pastorio, Mantova (IT); Paolo Betti, Brescia (IT)

(72) Inventors: Andrea Pastorio, Mantova (IT); Paolo Betti, Brescia (IT)

(73) Assignee: Finchimica S.p.A., Brescia (IT)

(21) Appl. No.: 14/534,001

(22) Filed: Nov. 5, 2014

Related U.S. Patent Documents

Reissue of:
(64) Patent No.: 8,304,559
Issued: Nov. 6, 2012
Appl. No.: 13/498,245
PCT Filed: May 26, 2011
PCT No.: PCT/IB2011/052304
§ 371 (c)(1),
(2) Date: Mar. 26, 2012
PCT Pub. No.: WO2012/004692
PCT Pub. Date: Jan. 12, 2012

(30) Foreign Application Priority Data

Jul. 7, 2010 (IT) ..... BS2010A0118

(51) Int. Cl.
*C07D 231/44* (2006.01)

(52) U.S. Cl.
CPC ..... *C07D 231/44* (2013.01); *Y02P 20/582* (2015.11)

(58) Field of Classification Search
CPC ..... C07D 231/44; Y02P 20/582; A01N 47/02
See application file for complete search history.

(56) References Cited

U.S. PATENT DOCUMENTS

| | | | |
|---|---|---|---|
| 3,928,372 | A | 12/1975 | Bochis et al. |
| 5,232,940 | A | 8/1993 | Hatton et al. |
| 6,013,761 | A | 1/2000 | Zierer et al. |
| 8,304,559 | B2 | 11/2012 | Pastorio et al. |
| 2013/0289283 | A1 | 10/2013 | Levin et al. |

FOREIGN PATENT DOCUMENTS

| | | | |
|---|---|---|---|
| AU | 2010100462 | A4 | 6/2010 |
| CN | 101250158 | A | 8/2008 |
| EP | 0295117 | A1 | 12/1988 |
| EP | 0565324 | A1 | 10/1993 |
| IL | 68284 | A | 4/1986 |
| IT | BS2010A0118 | | 7/2010 |
| WO | WO 01/30760 | | 5/2001 |
| WO | WO 01/30760 | A1 | 5/2001 |
| WO | WO 2007/122440 | | 11/2007 |
| WO | WO 2007/122440 | A1 | 11/2007 |
| WO | WO 2009/077853 | | 6/2009 |
| WO | WO 2012/004692 | A1 | 1/2012 |
| WO | WO 2012/007938 | A1 | 1/2012 |

OTHER PUBLICATIONS

Declaration—Bd.R. 203(b)—Paper 1, Patent Interference No. 105,995 (SGL), 2014, 7 pages.
Pastorio's Designation of Real Party-In-Interest—Paper 8, Patent Interference No. 105,995 (SGL), 2014, 2 pages.
Redeclaration—Bd.R. 203(c)—Paper 15, Patent Interference No. 105,995 (SGL), 2014, 3 pages.
Order—Miscellaneous—Bd.R. 104(a)—Paper 19, Patent Interference No. 105,995 (SGL), 2014, 4 pages.
Order—Miscellaneous—Bd.R. 104(a)—Paper 20, Patent Interference No. 105,995 (SGL), 2014, 3 pages.
Levin List of Proposed Motions—Paper 21, Patent Interference No. 105,995 (SGL), 2014, 6 pages.
Pastorio List of Proposed Motions—Paper 23, Patent Interference No. 105,995 (SGL), 2014, 3 pages.
Order—Motion Times—Bd.R. 104(c)—Paper 24, Patent Interference No. 105,995 (SGL), 2014, 7 pages.
Pastorio Motion 1 (for judgment based on no interference-in-fact)—Paper 25, Patent Interference No. 105,995 (SGL), 2014, 25 pages.
Pastorio Statutory Disclaimer in Patent Under 37 C.F.R. § 1.321(a)—Paper 26, Patent Interference No. 105,995 (SGL), 2014, 2 pages.
Order—Motion Times—Bd.R. 104(c)—Paper 38, Patent Interference No. 105,995 (SGL), 2014, 12 pages.
Errata—Paper 39, Patent Interference No. 105,995 (SGL), 2014, 2 pages.
Levin Substantive Motion 1 (for Judgment that Pastorio's involved Claims are Indefinite)—Paper 52, Patent Interference No. 105,995 (SGL), 2014, 28 pages.
Pastorio Contingent Motion 2 (to modify count and obtain benefit)—Paper 57, Patent Interference No. 105,995 (SGL), 2014, 20 pages.
(Continued)

*Primary Examiner* — Alan D Diamond
(74) *Attorney, Agent, or Firm* — Rothwell, Figg, Ernst & Manbeck, P.C.

(57) ABSTRACT

The present invention relates to a method for the preparation of the 5-amino-1-phenyl-3-cyano-4-trifluoromethyl sulfinyl pyrazole having the described general formula (I), particularly preferred for the synthesis of Fipronil I, through oxidation of a compound having the general formula (II) as follows:

(II)

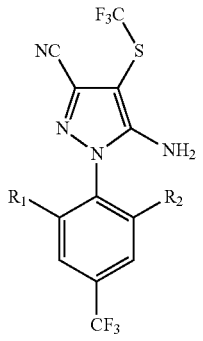

wherein $R_1$ and $R_2$ are independently hydrogen or halogen, and wherein the oxidizing agent is dichloroperacetic acid.

11 Claims, No Drawings

(56) References Cited

OTHER PUBLICATIONS

Decision—Miscellaneous Motion—Bd.R. 121(a)(3)—Paper 62, Patent Interference No. 105,995 (SGL), 2014, 5 pages.
Order—Authorizing Motion—Bd.R. 121(a)—Paper 76, Patent Interference No. 105,995 (SGL), 2014, 4 pages.
Levin Responsive Motion 2 (To Add Claim 11 Contingent Upon the Board Granting Pastorio Motion 1)—Paper 63, Patent Interference No. 105,995 (SGL), 2014, 29 pages.
Levin Amendment—Paper 71, Patent Interference No. 105,995 (SGL), 2014, 11 pages.
Pastorio Reissue Patent Application—Paper 72, Patent Interference No. 105,995 (SGL), 2014, 17 pages.
Pastorio Contingent Motion 3 (to add reissue application claims)—Paper 73, Patent Interference No. 105,995 (Sgl), 2014, 36 pages.
Order—Miscellaneous—Bd.R. 104(a)—Paper 80, Patent Interference No. 105,995 (SGL), 2014, 8 pages.
Pastorio Opposition 1—Paper 81, Patent Interference No. 105,995 (SGL), 2014, 34 pages.
Pastorio Opposition 2—Paper 110, Patent Interference No. 105,995 (SGL), 2014, 35 pages.
Levin Opposition 1—Paper 96, Patent Interference No. 105,995 (SGL), 2014, 45 pages.
Levin Opposition 2—Paper 97, Patent Interference No. 105,995 (SGL), 2014, 13 pages.
Levin Opposition 3—Paper 98, Patent Interference No. 105,995 (SGL), 2014, 38 pages.
Order—Miscellaneous—Bd.R. 104(a)—Paper 114, Patent Interference No. 105,995 (SGL), 2014, 9 pages.
Pastorio Reply 1—Paper 116, Patent Interference No. 105,995 (SGL), 2014, 35 pages.
Pastorio Reply 2—Paper 117, Patent Interference No. 105,995 (SGL), 2014, 17 pages.
Pastorio Reply 3—Paper 123, Patent Interference No. 105,995 (SGL), 2014, 27 pages.
Levin Reply 1—Paper 121, Patent Interference No. 105,995 (SGL), 2014, 37 pages.
Levin Reply 2—Paper 122, Patent Interference No. 105,995 (SGL), 2014, 39 pages.
Levin Miscellaneous Motion 3—Paper 130, Patent Interference No. 105,995 (SGL), 2014, 9 pages.
Pastorio Miscellaneous Opposition 3—Paper 136, Patent Interference No. 105,995 (SGL), 2015, 10 pages.
Levin Reply 3—Paper 140, Patent Interference No. 105,995 (SGL), 2015, 13 pages.
Order—Miscellaneous—Bd.R. 104(a)—Paper 141, Patent Interference No. 105,995 (SGL), 2015, 8 pages.
Order—Oral Argument—Bd. R. 124(a)—Paper 142, Patent Interference No. 105,995 (SGL), 2015, 3 pages.
Order—Oral Argument—Bd. R. 124(a)—Paper 143, Patent Interference No. 105,995 (SGL), 2015, 3 pages.
Decision on Motions—Bd. R. 121(a)—Paper 144, Patent Interference No. 105,995 (SGL), 2015, 28 pages.
Second Redeclaration—Bd.R 203(c)—Paper 145, Patent Interference No. 105,995 (SGL), 2015, 4 pages.
Order—Priority Times—Bd.R. 104(c)—Paper 146, Patent Interference No. 105,995 (SGL), 2015, 6 pages.
Errata—Paper 147, Patent Interference No. 105,995 (SGL), 2015, 2 pages.
Order—Authorizing Motion—37 C.F.R. § 41.121(a)—Paper 155, Patent Interference No. 105,995 (SGL), 2015, 4 pages.
Levin Motion No. 3 (Judgment Based on Priority of Invention)—Paper 174, Patent Interference No. 105,995 (SGL), 2015, 29 pages.
Levin Motion No. 4 (Judgment Based on Invalidity of the Pastorio Claims Over the Prior Art)—Paper 175, Patent Interference No. 105,995 (SGL), 2015, 38 pages.
Pastorio Motion 4 (for judgment based on priority)—Paper 177, Patent Interference No. 105,995 (SGL), 2015, 33 pages.
Pastorio Submission of Transcript of Sep. 29, 2015 Conference Call—Paper 217, Patent Interference No. 105,995 (SGL), 2015, 47 pages.
Decision—Motion—Bd.R. 121(a)(3)—Paper 219, Patent Interference No. 105,995 (SGL), 2015, 7 pages.
Pastorio Opposition 4—Paper 227, Patent Interference No. 105,995 (SGL), 2015, 44 pages.
Pastorio Opposition 3—Paper 229, Patent Interference No. 105,995 (SGL), 2015, 43 pages.
Levin Opposition 4—Paper 230, Patent Interference No. 105,995 (SGL), 2015, 30 pages.
Decision—Motion—Bd.R. 121(a)(3)—Paper 231, Patent Interference No. 105,995 (SGL), 2015, 6 pages.
Levin Reply 3—Paper 248, Patent Interference No. 105,995 (SGL), 2015, 42 pages.
Pastorio Reply 4—Paper 249, Patent Interference No. 105,995 (SGL), 2015, 34 pages.
Levin Reply 4—Paper 251, Patent Interference No. 105,995 (SGL), 2015, 41 pages.
Order—Authorizing Surreply—Bd.R. 104(a)—Paper 252, Patent Interference No. 105,995 (SGL), 2015, 6 pages.
Pastorio Surreply 4—Paper 253, Patent Interference No. 105,995 (SGL), 2015, 5 pages.
Decision—Miscellaneous Motion—Bd.R. 121(a)(3)—Paper 258, Patent Interference No. 105,995 (SGL), 2016, 4 pages.
Decision on Priority and Other Motions—Bd.R. 121(a)—Paper 259, Patent Interference No. 105,995 (SGL), 2016, 20 pages.
Judgment—Bd.R. 127(a)—Paper 260, Patent Interference No. 105,995 (SGL), 2016, 3 pages.
Levin Request for Rehearing (Regarding Levin Motion No. 4 and Judgment)—paper 261, Patent Interference No. 105,995 (SGL), 2016, 12 pages.
Order—Authorizing Opposition—Bd.R. 125(c)(4)—Paper 265, Patent Interference No. 105,995 (SGL), 2016, 4 pages.
Errata—Paper 266, Patent Interference No. 105,995 (SGL), 2016, 2 pages.
Pastorio Opposition to Levin Request for Rehearing—Paper 267, Patent Interference No. 105,995 (SGL), 2016, 11 pages.
Decision on Request for Rehearing—Bd.R. 125(c) and 127(d)—Paper 271, Patent Interference No. 105,995 (SGL), 2016, 9 pages.
Adama Petition for Inter Partes Review of U.S. Pat. No. 8,304,559—Paper 2, IPR2016-00577, 2016, 66 pages.
Patent Owner Preliminary Response to Petition for Inter Partes Review—Paper 6, IPR2016-00577, 2016, 35 pages.
Decision—Institution of Inter Partes Review—37 C.F.R. § 42.108—Paper 7, IPR2016-00577, 2016, 18 pages.
Scheduling Order—Paper 8, IPR2016-00577, 2016, 6 pages.
Patent Owner's Request for Partial Rehearing of the Board's Decision Instituting Inter Partes Review—Paper 9, IPR2016-00577, 2016, 18 pages.
Petitioner's Request for Partial Rehearing—Paper 10, IPR2016-00577, 2016, 10 pages.
Decision—Request for Rehearing—37 C.F.R. § 42.71(a)—Paper 11, IPR2016-00577, 2016, 6 pages.
Order Modifying Scheduling Order—Paper 16, IPR2016-00577, 2016, 3 pages.
Decision—Request for Rehearing—37 C.F.R. § 42.71(a)—Paper 17, IPR2016-00577, 2016, 5 pages.
Second Order Modifying Scheduling Order—Paper 18, IPR2016-00577, 2016, 7 pages.
Patent Owner Response—Paper 19, IPR2016-00577, 2016, 61 pages.
Order—Conduct of the Proceeding—37 CFR 42.5(a)—Paper 20, IPR2016-00577, 2016, 8 pages.
Petitioner's Reply to Patent Owner Response—Paper 22, IPR2016-00577, 2016, 38 pages.
Order—Oral Argument—Paper 25, IPR2016-00577, 2017, 3 pages.
Petitioner's Demonstratives for Oral Argument on Feb. 14, 2017—Paper 26, IPR2016-00577, 2017, 12 pages.
Patent Owner's Corrected Submission of Demonstrative Exhibits for Feb. 14, 2017 Oral Hearing—Paper 28, IPR2016-00577, 2017, 18 pages.

(56) References Cited

OTHER PUBLICATIONS

Transcript of Feb. 14, 2017 Oral Hearing—Paper 29, IPR2016-00577, 2017, 45 pages.
Final Written Decision—35 U.S.C. § 318(a) and 37 C.F.R. § 42.73—Paper 30, IPR2016-00577, 2017, 22 pages.
Patent Owner's Notice of Appeal—Paper 32, IPR2016-00577, 2017, 28 pages.
Notice of Docketing—Dkt. 1, Fed. Cir. Appeal No. 17-2195, 2017, 29 pages.
Appellant's Opening Brief—Dkt. 17 & 18, Fed. Cir. Appeal No. 17-2195, 2017, 102 pages.
Corrected Brief of Appellee Adama Makhteshim Ltd.—Dkt. 25 & 27, Fed. Cir. Appeal No. 17-2195, 2017, 64 pages.
Corrected Appellant's Reply Brief—Dkt. 33 & 34, Fed. Cir. Appeal No. 17-2195, 2018, 40 pages.
Joint Appendix—Dkt. 36 & 37, Fed. Cir. Appeal No. 17-2195, 2018, 367 pages.
Judgment—Dkt. 48, Fed. Cir. Appeal No. 17-2195, 2018, 5 pages.
Appellant's Combined Request for Rehearing and Rehearing En Banc—Dkt. 53, Fed. Cir. Appeal No. 17-2195, 2018, 25 pages.
Order Denying Petition for Panel Rehearing and Rehearing En Banc—Dkt. 55, Fed. Cir. Appeal No. 17-2195, 2018, 2 pages.
Corrected Order Denying Petition for Panel Rehearing and Rehearing En Banc—Dkt. 56, Fed. Cir. Appeal No. 17-2195, 2018, 2 pages.
Mandate—Dkt. 57, Fed. Cir. Appeal No. 17-2195, 2018, 1 page.
Declaration of Barry M. Trost, Ph.D., Patent Interference No. 105,995 (SGL), May 23, 2014, 20 pages (Exhibit 2003).
Curriculum vitae of Barry M. Trost, Ph.D., Patent Interference No. 105,995 (SGL), (Exhibit 2004), May 23, 2014, 81 pages (Exhibit 2004).
Kaczorowska et al.,"Oxidation of Sulfides to Sulfoxides. Part 2: Oxidation by Hydrgen Peroxide," Tetrahedron, 61: 8315-8327 (2005) (Exhibit 2005).
Oda et al., "Some Researches on the Chemistry of Dimethyl Sulfoxide and Related Compounds," Bull. Inst. Chem. Res., Kyoto Univ., 47(5): 480-521 (1970) (Exhibit 2006).
Kenney et al., "An Acid-catalyzed Cleavage of Sulfoxides," J. Am. Chem. Soc., 83: 4019-4022 (1961) (Exhibit 2007).
Jerry March, Advanced Organic Chemistry: Reactions, Mechanisms, and Structure (Fourth Ed. 1992) at pp. 887-888, 1236 (Exhibit 2008).
Jerry March, Advanced Organic Chemistry: Reactions, Mechanisms, and Structure (Fourth Ed. 1992) at pp. 1201-1203 (Exhibit 2013).
Overberger et al., "Kinetics and Mechanism of the Oxidation of p,p'-Dichlorobenzyl Sulfide by Hydrogen Peroxide," J. Am. Chem. Soc., 1953, 75(19), 4783-4787 (Exhibit 2014).
Deposition transcript of Gordon W. Gribble, Ph.D., Patent Interference No. 105,995 (SGL), Aug. 29, 2014, 103 pages (Exhibit 2015).
Deposition transcript of Barry M. Trost, Ph.D., Patent Interference No. 105,995 (SGL), Oct. 13, 2014, 98 pages (Exhibit 2016).
Second Declaration of Barry M. Trost, Ph.D., Patent Interference No. 105,995 (SGL), Oct. 31, 2014, 22 pages (Exhibit 2018).
Golchoubian et al., "Effective Oxidation of Sulfides to Sulfoxides with Hydrogen Peroxide under Transition-Metal Free Conditions," Molecules, 2007, 12, 304-311 (Exhibit 2019).
Ravikumar et al., "Role of Hexafluoro-2-propanol in Selective Oxidation of Sulfide to Sulfoxide: Efficient Preparation of Glycosyl Sulfoxides," Eur. J. Org. Chem., 1998, 2937-2940 (Exhibit 2020).
Lakouraj et al., "Ion Exchange Resin Catalyzed Selective Oxidation of Sulfides to Sulfoxides Using Hydrogen Peroxide," Monatsheft fur Chemie, 2007, 138, 83-88 (Exhibit 2021).
Ex parte Viola, 2008 U.S. Pat. App. Lexis 5135 (BPAI Mar. 12, 2008), 3 pages (Exhibit 2023).
Ex parte Stam, 2012 WL 1961900 (BPAI May 24, 2012), 7 pages (Exhibit 2024).
Ex parte Koninklijke Philips Electronics N.V., 2013 WL 2139858 (BPAI Apr. 24, 2013), 6 pages (Exhibit 2025).
Prosecution history for U.S. Appl. No. 13/498,245, filed Mar. 26, 2012, 450 pages (Exhibit 2027).
Notice of Allowance filed on Jul. 12, 2012, in U.S. Appl. No. 13/498,245, 8 pages (Exhibit 2028).
The Merck Index—An Encyclopedia of Chemicals, Drugs, and Biologics, Merck & Co., Inc. p. 3043 (11th ed. 1989), 3 pages (Exhibit 2029).
International Preliminary Report on Patentability filed on Jan. 15, 2013, in International Application No. PCT/IL2011/000546, 8 pages. (Exhibit 2030).
Letter from Micaela Nadia Modiano to the Examining Division of the EPO, dated Sep. 20, 2013, in European Patent Application No. 11752348.0-1462, 3 pages (Exhibit 2031).
Suggestion of Interference Pursuant to 37 C.F.R. § 41.202 filed on Jun. 25, 2013, in U.S. Appl. No. 13/926,389, 40 pages (Exhibit 2032).
*Kaneko* v. *Wengel*, 2014 Pat. App. Lexis 3279, at *64 (PTAB May 29, 2014), 21 pages (Exhibit 2033).
Email from Levin Counsel, Patent Interference No. 105,995 (SGL), Dec. 1, 2014, 1 page (Exhibit 2034).
Oct. 1, 2009 purchase order confirmation; English translation; certifications of Translation, Patent Interference No. 105,995 (SGL), 6 pages (Exhibit 2035).
Oct. 6, 2009 purchase order; Oct. 15, 2009 invoice with stamp of receipt, and Oct. 1, 2009 shipping document; English translations; certification of translation, Patent Interference No. 105,995 (SGL), 9 pages (Exhibit 2036).
Dec. 22, 2009 experiment report PS/43/2009/PB; English translation; certification of translation, Patent Interference No. 105,995 (SGL), 5 pages (Exhibit 2037).
Dec. 22, 2009 experiment report PS/43/2009/PB—Mettler Toledo Report, Patent Interference No. 105,995 (SGL), 6 pages (Exhibit 2038).
Dec. 22, 2009 experiment report PS/44/2009/PB; English translation; certification of translation, Patent Interference No. 105,995 (SGL), 5 pages (Exhibit 2039).
Dec. 23, 2009 experiment report PS/45/2009/PB; English translation; certification of translation, Patent Interference No. 105,995 (SGL), 5 pages (Exhibit 2040).
Jan. 4, 2010 experiment report PS/01/2010/PB; English translation; certification of Translation, Patent Interference No. 105,995 (SGL), 5 pages (Exhibit 2041).
Jan. 7, 2010 experiment report PS/03/2010/PB; English translation; certification of Translation, Patent Interference No. 105,995 (SGL), 5 pages (Exhibit 2042).
Email correspondence between Andrea Pastorio and Giacomo Ravetta on Feb. 15, 2010 (redacted) with attached document titled @I0139145. Finchimica—Testo BR IT—Fipronil revisione J . . . ; English translation of redacted email and attached document; certifications for translations, Patent Interference No. 105,995 (SGL), 38 pages (Exhibit 2043).
Jan. 12, 2010 experiment report PS/04/2010/PB; English translation; certification of translation, Patent Interference No. 105,995 (SGL), 5 pages (Exhibit 2044).
Jan. 21, 2010 email; English translation; certification of translation, Patent Interference No. 105,995 (SGL), 5 pages (Exhibit 2045).
Jan. 21, 2010 document titled Relazione fipronil x pellegri.doc (redacted); English translation; certification of translation, Patent Interference No. 105,995 (SGL), 67 pages (Exhibit 2046).
Jan. 26, 2010 experiment report PS/07/2010/PB; English translation; certification of translation, Patent Interference No. 105,995 (SGL), 5 pages (Exhibit 2047).
Jan. 26, 2010 experiment report PS/02/2010/RP; English translation; certification of translation, Patent Interference No. 105,995 (SGL), 7 pages (Exhibit 2048).
Chromatograms for Jan. 26, 2010 experiment report PS/02/2010/RP, Patent Interference. No. 105,995 (SGL), 7 pages (Exhibit 2049).
Jan. 28, 2010 experiment report PS/08/2010/PB; English translation; certification of translation, Patent Interference No. 105,995 (SGL), 5 pages (Exhibit 2050).
Jan. 28, 2010 experiment report PS/03/2010/RP; English translation; certification of translation, Patent Interference No. 105,995 (SGL), 5 pages (Exhibit 2051).

(56) References Cited

OTHER PUBLICATIONS

Feb. 1, 2010 experiment report PS/10/2010/PB; English translation; certification of translation, Patent Interference No. 105,995 (SGL), 7 pages (Exhibit 2052).
Feb. 2, 2010 experiment report PS/04/2010/RP; English translation; certification of translation, Patent Interference No. 105,995 (SGL), 7 pages (Exhibit 2053).
Feb. 4, 2010 experiment report PS/05/2010/RP; English translation; certification of translation, Patent Interference No. 105,995 (SGL), 9 pages (Exhibit 2054).
Feb. 5, 2010 chromatograms for experiment report PS/05/2010/RP, Patent Interference No. 105,995 (SGL), 6 pages (Exhibit 2055).
Feb. 3-10, 2010 chromatograms for experiment report PS/05/2010/RP, Patent. Interference No. 105,995 (SGL), 14 pages (Exhibit 2056).
Feb. 5, 2010 experiment report PS/06/2010/RP; English translation; certification of translation, Patent Interference No. 105,995 (SGL), 5 pages (Exhibit 2057).
Feb. 8, 2010 experiment report PS/12/2010/PB; English translation; certification of translation, Patent Interference No. 105,995 (SGL), 5 pages (Exhibit 2058).
Feb. 11, 2010 experiment report PS/02/2010/CM; English translation; certification of translation, Patent Interference No. 105,995 (SGL), 22 pages (Exhibit 2060).
Excerpts from laboratory notebook of Claudia Mora; English translation; certification of translation, Patent Interference No. 105,995 (SGL), Nov. 10, 2015, 46 pages (Exhibit 2062).
Curriculum Vitae of Claudia Mora, Patent Interference No. 105,995 (SGL), Aug. 25, 2015, 3 pages (Exhibit 2063).
Curriculum Vitae of Roberto Pellegri, Patent Interference No. 105,995 (SGL), Aug. 25, 2015, 1 page (Exhibit 2064).
Curriculum Vitae of Paolo Betti, Ph.D., Patent Interference No. 105,995 (SGL), Aug. 25, 2015, 3 pages (Exhibit 2065).
Curriculum Vitae of Andrea Pastorio, Patent Interference No. 105,995 (SGL), Aug. 25, 2015, 3 pages (Exhibit 2066).
Declaration of Maria Grazia Renzi and Rodolfo Peveri, Patent Interference No. 105,995 (SGL), Aug. 25, 2015, 3 pages (Exhibit 2068).
Excerpts from laboratory notebook of Roberto Pellegri; English translation; certification of translation, Patent Interference No. 105,995 (SGL), Aug. 15, 2015, 31 pages (Exhibit 2070).
Jan. 6, 2010 experiment report PS/02/2010/PB; English translation; certification of Translation, Patent Interference No. 105,995 (SGL), 5 pages (Exhibit 2071).
Declaration of Giacomo Ravetta, Patent Interference No. 105,995 (SGL), Aug. 25, 2015, 3 pages (Exhibit 2072).
Declaration of Paolo Betti, Ph.D., Patent Interference No. 105,995 (SGL), Aug. 25, 2015, 12 pages (Exhibit 2073).
Declaration of Andrea Pastorio, Patent Interference No. 105,995 (SGL), Aug. 25, 2015, 13 pages (Exhibit 2074).
Declaration of Claudia Mora, Patent Interference No. 105,995 (SGL), Aug. 25, 2015, 11 pages (Exhibit 2075).
Declaration of Roberto Pellegri, Patent Interference No. 105,995 (SGL), Aug. 25, 2015, 10 pages (Exhibit 2077).
Substituent Effects, Chapter 12: Reactions of Arenes. Electrophilic Aromatic Substitution (McGraw Hill) found at: http://www.mhhe.com/physsci/chemistry/carey/student/olc/ch12substituenteffects.html, Sep. 16, 2015, 6 pages (Exhibit 2078).
Siddiqui et al., "Thiazoles: A Valuable Insight into the Recent Advances and Biological Activities," Int'l J. Pharm. Sci.& Drug Res., 2009; 1(3): 136-143, (Exhibit 2079).
Declaration of David P. Gitkos, Patent Interference No. 105,995 (SGL), Sep. 30, 2015, 77 pages (Exhibit 2080).
Second Declaration of Roberto Pellegri, Patent Interference No. 105,995 (SGL), Sep. 30, 2015, 3 pages (Exhibit 2081).
Second Declaration of Claudia Mora, Patent Interference No. 105,995 (SGL), Sep. 30, 2015, 3 pages (Exhibit 2082).
Deposition transcript of Gordon W. Gribble, Ph.D., Patent Interference No. 105,995 (SGL), Sep. 17, 2015, 102 pages (Exhibit 2083).
Letter, dated Sep. 20, 2013, filed in European Patent Application No. 11752348.0-1462, Patent Interference No. 105,995 (SGL), 10 pages (Exhibit 2084).
Declaration of Dennis P. Curran, Ph.D., Patent Interference No. 105,995 (SGL), Oct. 6, 2015, 28 pages (Exhibit 2085).
Curriculum Vitae of Dennis P. Curran, Ph.D., Patent Interference No. 105,995 (SGL), Sep. 3, 2015, 58 pages (Exhibit 2086).
Ex parte Yu-Piao Wang, Appeal 2011-011246, 2013 Pat. App. Lexis 8918 (P.T.A.B. Dec. 2, 2013), 4 pages (Exhibit 2087).
Ex parte Woodruff, No. 2001-1055, 2003 WL 25277886 (B.P.A.I. Sep. 30, 2003), 3 pages (Exhibit 2088).
*Chatterjee* v. *Tabor*, No. 105,292, slip op. (B.P.A.I. Mar. 15, 2007), 32 pages (Exhibit 2089).
Information Disclosure Statement, filed on June 25, 2013, in U.S. Appl. No. 13/926,389, 7 pages (Exhibit 2090).
*Synopsys, Inc.* v. *Mentor Graphics Corp.*, No. 2014-1516, 2016 U.S. App. Lexis 2250 (Fed. Cir. Feb. 10, 2016), 26 pages. (Exhibit 2091).
Declaration of Gordon W. Gribble, Ph.D., Patent Interference No. 105,995 (SGL), Jul. 18, 2014, 11 pages (Exhibit 1001).
Curriculum vitae of Gordon W. Gribble, Ph.D., Patent Interference No. 105,995 (SGL), Jul. 18, 2014, 80 pages (Exhibit 1002).
First Preliminary Amendment filed in connection with U.S. Appl. No. 13/498,245, Patent Interference No. 105,995 (SGL), Mar. 26, 2012, 7 pages (Exhibit 1003).
Renewed Request for Patent Prosecution Highway and Response to Decision to Dismiss Petition for Patent Prosecution Highway filed in connection with U.S. Appl. No. 13/498,245, Patent Interference No. 105,995 (SGL), Jun. 18, 2012, 5 pages (Exhibit 1004).
Written Opinion of the International Searching Authority issued in connection with PCT International Application No. PCT/IB2011/052304 (the Pastorio PCT), Patent Interference No. 105,995 (SGL), dated Jul. 18, 2014, 8 pages (Exhibit 1005).
Second Preliminary Amendment filed in connection with U.S. Appl. No. 13/498,245, Patent Interference No. 105,995 (SGL), Jun. 18, 2012, 5 pages (Exhibit 1006).
Notice of Allowance, including Notice of Allowability issued in connection with U.S. Appl. No. 13/498,245, Patent Interference No. 105,995 (SGL), dated Jul. 12, 2012, 8 pages (Exhibit 1007).
Comments on Statement of Reasons for Allowance filed in connection with U.S. Appl. No. 13/498,245, Patent Interference No. 105,995 (SGL), Oct. 1, 2012, 2 pages (Exhibit 1008).
Chapter 7 of *Modern Oxidation Methods*, J.E. Backvall, ed., Wiley-VCH Verlag GmbH & Co. KGaA (2004), 39 pages (Exhibit 1009).
U.S. Appl. No. 13/926,389, filed Jun. 25, 2013, Patent Interference No. 105,995 (SGL), 14 pages (Exhibit 1010).
U.S. Appl. No. 61/363,366, Patent Interference No. 105,995 (SGL), filed Jul. 12, 2019, 22 pages (Exhibit 1012).
Second Declaration of Gordon W. Gribble, Ph.D., Patent Interference No. 105,995 (SGL), Jul. 25, 2014, 13 pages (Exhibit 1013).
Daniel Swern, "Organic Peracids," Chem. Rev., 1949, 45 (1), pp. 1-68 (Exhibit 1015).
Transcript of Oct. 13, 2014 Deposition of Barry M. Trost, Ph.D., Patent Interference No. 105,995 (SGL), 98 pages (Exhibit 1017).
Third Declaration of Gordon W. Gribble, Ph.D., Patent Interference No. 105,995 (SGL), Oct. 31, 2014, 20 pages (Exhibit 1018).
Transcript of Aug. 29, 2014 Deposition of Gordon W. Gribble, Ph.D., Patent Interference No. 105,995 (SGL), 93 pages (Exhibit 1020).
*Perry's Chemical Engineers' Handbook*, Sixth Edition, R.H. Perry et al., eds. McGraw-Hill Book Co. (1984), pp. 4-4 to 4-5, Patent Interference No. 105,995 (SGL), 6 pages (Exhibit 1021).
Fourth Declaration of Gordon W. Gribble, Ph.D., Patent Interference No. 105,995 (SGL), Oct. 31, 2014, 18 pages (Exhibit 1022).
Federal Register vol. 69, No. 155, pp. 49960-50020 (Aug. 12, 2004), 62 pages (Exhibit 1025).
Chinese Patent Application Publication No. CN 101250158A, including English translation, filed with a Dec. 30, 2013 Third Party Submission Under 37 C.F.R. § 1.290 in U.S. Appl. No. 13/926,389, Patent Interference No. 105,995 (SGL), filed Apr. 2, 2008, 12 pages (Exhibit 1026).
Levin Objection to Second Declaration of Barry M. Trost, Ph.D. (Ex. 2018) Served by Pastorio on Oct. 31, 2014, Patent Interference No. 105,995 (SGL), 3 pages (Exhibit 1027).

(56) References Cited

OTHER PUBLICATIONS

AML Chemistry report for May 2010 by Dr. Michael Grabarnick, with English language translation, Patent Interference No. 105,995 (SGL), 3 pages (Exhibit 1029).
AML Fipronil Project Laboratory Notebook No. 424, p. 119 with verified English language translation, Patent Interference No. 105,995 (SGL), May 23, 2010, 3 pages (Exhibit 1030).
AML Fipronil Project Laboratory Notebook No. 424, p. 120 with verified English language translation, Patent Interference No. 105,995 (SGL), May 23, 2010, 3 pages (Exhibit 1031).
AML Fipronil Project Laboratory Notebook No. 424, p. 138 with English language translation, Patent Interference No. 105,995 (SGL), Jun. 6, 2010, 3 pages (Exhibit 1032).
AML analytical report for Sample 424-138-2, dated Jun. 7, 2010, by Michael Mogilnitsky, M.Sc., with English language translation, Patent Interference No. 105,995 (SGL), 12 pages (Exhibit 1033).
AML Fipronil Project Laboratory Notebook No. 424, p. 152 with English language translation, Patent Interference No. 105,995 (SGL), Jun. 15, 2010, 2 pages (Exhibit 1034).
Jun. 13, 2010 email from Dr. Michael Grabarnick to Michal Telnoy with invention disclosure attached, Patent Interference No. 105,995 (SGL), 7 pages (Exhibit 1035).
Jun. 30, 2010 email from Benjamin Schneider to Bertha Fuxman with invention disclosure document attached, Patent Interference No. 105,995 (SGL), 7 pages (Exhibit 1036).
Declaration of Michael Grabarnick, Ph.D., Patent Interference No. 105,995 (SGL), Aug. 16, 2015, 12 pages (Exhibit 1039).
Declaration of Michael Mogilnitsky, M.Sc., Patent Interference No. 105,995 (SGL), Aug. 16, 2015, 5 pages (Exhibit 1041).
Fifth Declaration of Gordon W. Gribble, Ph.D., Patent Interference No. 105,995 (SGL), Aug. 17, 2015, 9 pages (Exhibit 1042).
Sigma-Aldrich Charges Summary, Patent Interference No. 105,995 (SGL), May 18, 2010, 1 page (Exhibit 1043).
Sixth Declaration of Gordon W. Gribble, Ph.D., Patent Interference No. 105,995 (SGL), Aug. 17, 2015, 36 pages (Exhibit 1044).
Declaration of Anat Levin, Ph.D., Patent Interference No. 105,995 (SGL), Aug. 17, 2015, 4 pages (Exhibit 1045).
H. Harry Szmant, Chapter 16, "Chemistry of the Sulfoxide Group," *Organic Sulfur Compounds* (1961): 154-69 (Exhibit 1046).
Dennis P. Curran and Sung-Bo Ko. "Synthesis of Optically Active a-Hydroxy Lactones by Sharpless Asymmetric Dihydroxylations of Ketene Acetals, Enol Ethers, and Ene Lactones." *The Journal of Organic Chemistry J. Org. Chem. 59.21* (1994): 6139-141 (Exhibit 1047).
Dennis P. Curran, Ulf Diederichsen, and Michael Palovich. "Radical Cyclizations of Acylgermanes. New Reagent Equivalents of the Carbonyl Radical Acceptor Synthon." *J. Am. Chem. Soc. Journal of the American Chemical Society* 119.21 (1997): 4797-804 (Exhibit 1048).
Ali Ates and Dennis P. Curran. "Synthesis of Enantioenriched Axially Chiral Anilides from Atropisomerically Enriched Tartarate Ortho-Anilides." *J. Am. Chem. Soc. Journal of the American Chemical Society* 123.21 (2001): 5130-131 (Exhibit 1049).
Transcript of Sep. 17, 2015 Deposition of Gordon W. Gribble, Ph.D., Patent Interference No. 105,995 (SGL), 103 pages (Exhibit 1050).
Inventor Declaration of Anat Levin in U.S. Appl. No. 13/926,389, Patent Interference No. 105,995 (SGL), Jul. 7, 2013, 3 pages (Exhibit 1051).
Transcript of Oct. 27, 2015 Deposition of Dennis P. Curran, Ph.D., Patent Interference No. 105,995 (SGL), 158 pages (Exhibit 1052).
Decision on Priority and other Motions—Bd. R. 121(a), filed on Mar. 16, 2016, in Interference No. 105,995 (Paper 259), IPR2016-00577, 20 pages (Exhibit 2002).
Levin List of Proposed Motions, filed on May 7, 2014, in Interference No. 105,995 (Paper 21), IPR2016-00577, 6 pages (Exhibit 2003).
Order—Motion Times—Bd. R. 104(c), filed on May 30, 2014, in Interference No. 105,995 (Paper 38), IPR2016-00577, 12 pages (Exhibit 2004).
Email from Gary Gershik, counsel for Levin, to the Patent Trial and Appeal Board, dated Jul. 31, 2015, IPR2016-00577, 1 page (Exhibit 2005).
Order—Authorizing Motion—37 C.F.R. § 41.121(a), filed on Aug. 4, 2015, in Interference No. 105,995 (Paper 155), IPR2016-00577, 4 pages (Exhibit 2006).
Information Disclosure Statement, filed on June 25, 2013, in U.S. Appl. No. 13/926,389, IPR2016-00577, 8 pages (Exhibit 2007).
Levin Motion No. 4 (Judgment Based on Invalidity [sic] of the Pastorio Claims over the Prior Art), filed on Aug. 17, 2015, in Interference No. 105,995 (Paper 175), IPR2016-00577, 38 pages (Exhibit 2008).
Levin Reply 4 (Judgment Based on Invalidity [sic] of the Pastorio Claims over the Prior Art), filed on Nov. 10, 2015, in Interference No. 105,995 (Paper 251), IPR2016-00577, 41 pages (Exhibit 2009).
Pastorio Opposition 4, filed on Oct. 16, 2015, in Interference No. 105,995 (Paper 227), IPR2016-00577, 44 pages (Exhibit 2010).
Pastorio Surreply 4, filed on Nov. 24, 2015, in Interference No. 105,995 (Paper 253), IPR2016-00577, 5 pages (Exhibit 2011).
Decision on Motions—Bd. R. 121(a), filed on Jun. 26, 2015, in Interference No. 105,995 (Paper 144), IPR2016-00577, 28 pages (Exhibit 2012).
Order—Authorizing Surreply—Bd. R. 104(a), filed on Nov. 19, 2015, in Interference No. 105,995 (Paper 252), IPR2016-00577, 6 pages (Exhibit 2014).
*Lee* v. *Dryja*, Interference No. 105,182, 2005 Pat. App. Lexis 38 (B.P.A.I. Dec. 7, 2005), 24 pages (Exhibit 2015).
Acros Organics Material Safety Data Sheet for Trichloroacetic acid, IPR2016-00577, filed as exhibit on Aug. 31, 2016, 3 pages (Exhibit 2016).
Sigma-Aldrich Material Safety Data Sheet for Dichloromethane, IPR2016-00577, Jun. 28, 2016, 10 pages (Exhibit 2017).
Sigma-Aldrich Material Safety Data Sheet for Dichloroacetic acid IPR2016-00577, Jun. 19, 2015, 8 pages (Exhibit 2018).
Fourth Declaration of Gordon W. Gribble, Ph.D., filed in Interference No. 105,995 (Levin Exhibit 1022), IPR2016-00577, Oct. 31, 2014, 19 pages (Exhibit 2019).
Curriculm Vitae of Dennis P. Curran, Ph.D., IPR2016-00577, Oct. 31, 2014, 55 pages (Exhibit 2020).
Deposition Transcript of Gordon Gribble, Ph.D., dated Aug. 3, 2016, IPR2016-00577, 98 pages (Exhibit 2021).
Hawley's Condensed Chemical Dictionary, p. 1032 (Richard J. Lewis, Sr. ed., John Wiley & Sons, Inc., 14$^{th}$ ed., 2001), 3 pages (Exhibit 2023).
Organic Chemistry: An Advanced Treatise, vol. II, pp. 1726-1739 (Henry Gilman ed., John Wiley & Sons, Inc., 2d ed., 1943), 17 pages (Exhibit 2024).
Ullman's Encyclopedia of Industrial Chemistry, Chloroacetic Acids, pp. 473-490 (Koenig et al., John Wiley & Sons, Inc., 2014), 18 pages (Exhibit 2025).
Declaration of Dennis Curran, Ph.D., IPR2016-00577, Aug. 31, 2016, 45 pages (Exhibit 2026).
Christian Reichardt, "Solvatochromic Dyes as Solvent Polarity Indicators," Chem. Rev., 94(8):2319-2358 (1994) (Exhibit 2027).
Sixth Declaration of Gordon W. Gribble, Ph.D., filed in Interference No. 105,995 (Levin Exhibit 1044), IPR2016-00577, Aug. 17, 2015, 37 pages (Exhibit 2028).
Declaration of Gordon W. Gribble, Ph.D., IPR2016-00577, Feb. 4, 2016, 50 pages (Exhibit 1010).
Curriculum Vitae of Gordon W. Gribble, Ph.D., IPR2016-00577, Feb. 4, 2016, 82 pages (Exhibit 1011).
Chapter 7 of Modern Oxidation Methods, J.E. Backvall, ed., Wiley-VCH Verlag GmbH & Co. KGaA (2004) 39 pages (Exhibit 1014).
A. Treiber, "Mechanism of the Aromatic Hydroxylation of Thiophene by Acid-Catalyzed Peracid Oxidation" J. Org. Chem. 2002, 67, 7261-7266 (Exhibit 1016).
C.G. Overberger and R.W. Cummins, J Am. Chem. Soc., 1953, 75 (19), pp. 4783-4787 (Exhibit 1017).
H.C. Brown, D.H. McDaniel, and O.Haflinger, "Determination of Organic Structures by Physical Methods, vol. 1" E.A. Braude and F.C. Nachold, Eds., Academic Press, NY, 1955, p. 567 (Exhibit 1018).

(56) References Cited

OTHER PUBLICATIONS

"Dissociation Constants of Organic Acids and Bases" CRC Handbook of Chemistry and Physics, 91th Edition, Section 8, pp. 42-51, Jun. 2010 (Exhibit 1019).
Thermo Fisher Scientific, meta-Chloroperbenzoic Acid Technical Data Sheet, revision Sep. 26, 2012, 4 pages (Exhibit 1020).
Acros Organics, Safety Data Sheet for Dichloroacetic acid, revision Oct. 7, 2014, 7 pages (Exhibit 1021).
Paper 1—Declaration of Interference filed Feb. 6, 2014 in Interference No. 105,995, IPR2016-00577, 7 pages (Exhibit 1022).
Paper 21—Levin List of Proposed Motions filed May 7, 2014 in Interference No. 105,995, IPR2016-00577, 6 pages (Exhibit 1023).
Paper 25—Pastorio Motion 1 (for judgment based on no interference-in-fact) filed May 23, 2014 in Interference No. 105,995, IPR2016-00577, 25 pages (Exhibit 1024).
Paper 26—Statutory Disclaimer filed on May 23, 2014 in Interference No. 105,995, IPR2016-00577, 2 pages (Exhibit 1025).
Paper 38—Order—Motion Times filed May 30, 2014 in Interference No. 105,955, IPR2016-00577, 12 pages (Exhibit 1026).
Paper 116—Pastorio Reply 1 (for judgment based on no interference-in-fact) filed Dec. 19, 2014 in Interference No. 105,995, IPR2016-00577, 35 pages (Exhibit 1027).
Paper 144—Decision on Motions filed Jun. 26, 2015 in Interference No. 105,995, IPR2016-00577, 28 pages (Exhibit 1028).
Paper 155—Order Authorizing Motion filed Aug. 4, 2015 in Interference No. 105,995, IPR2016-00577, 4 pages (Exhibit 1029).
Paper 175—Levin Motion 4 (for judgment Based on Invalidity of the Pastorio Claims over the Prior Art) filed Aug. 17, 2015 in Interference No. 105,995, IPR2016-00577, 38 pages (Exhibit 1030).
Paper 177—Pastorio Motion 4 (for judgement based on priority) filed Aug. 25, 2015 in Interference No. 105,995, IPR2016-00577, 33 pages (Exhibit 1031).
Dec. 22, 2009 experiment report PS/43/2009/PB; English translation; certification of translation; submitted as Exhibit 2037 in Interference No. 105,995, IPR2016-00577, 5 pages (Exhibit 1032).
Dec. 22, 2009 experiment report PS/44/2009/PB; English translation; certification of translation; submitted as Exhibit 2039 in Interference No. 105,995, IPR2016-00577, 5 pages (Exhibit 1033).
Dec. 23, 2009 experiment report PS/45/2009/PB; English translation; certification of translation; submitted as Exhibit 2040 in Interference No. 105,995, IPR 2016-00577, 5 pages (Exhibit 1034).
Paper 227—Pastorio Opposition 4 filed Oct. 6, 2015 in Interference No. 105,995, IPR2016-00577, 44 pages (Exhibit 1035).
Paper 251—Levin Reply 4 filed Nov. 10, 2015 in Interference No. 105,995, IPR2016-00577, 41 pages (Exhibit 1036).
Transcript of Oct. 27, 2015 Deposition of Dennis P. Curran, Ph.D. submitted as Exhibit 1052 in Interference No. 105,995, IPR2016-00577, 158 pages (Exhibit 1037).
"Fluoroacetate Toxicity" J. Chem. Ed. 1973, 50, 460, 3 pages (Exhibit 1038).
Transcript of Oct. 27, 2016 Deposition of Dennis P. Curran, Ph.D., IPR2016-00577, 159 pages (Exhibit 1039).
Declaration of Gordon W. Gribble, Ph.D., dated Jul. 18, 2014, filed Jul. 18, 2014 in Patent Interference No. 105,995.
Curriculum vitae of Gordon W. Gribble, Ph.D., filed Jul. 18, 2014 in Patent Interference No. 105,995.
Chapter 7 of *Modern Oxidation Methods*, J.E. Backvall, ed., Wlley-VCH Verlag GmbH & Co. KGaA (2004).
Transcript of Aug. 29, 2014 Deposition of Gordon W. Gribble, Ph.D., filed Oct. 31, 2014 in Patent Interference No. 105,995.
Fourth Declaration of Gordon W. Gribble, Ph.D., dated Oct. 31, 2014, filed Oct. 31, 2014 in Patent Interference No. 105,995.
Declaration of Barry M. Trost, Ph.D., dated May 23, 2014, filed May 23, 2014 in Patent Interference No. 105,995.
*Curriculum vitae* of Barry M. Trost, Ph.D., filed May 23, 2014 in Patent Interference No. 105,995.
Deposition transcript of Barry M. Trost, Ph.D., dated Oct. 13, 2014, filed Oct. 31, 2014 in Patent Interference No. 105,995.
Second Declaration of Barry M. Trost, Ph.D., dated Oct. 31, 2014, filed Oct. 31, 2014 in Patent Interference No. 105,995.
Levin Substantive Motion 1, filed Jul. 18, 2014 in Patent Interference No. 105,995.
Pastorio Contingent Motion 3, filed Jul. 25, 2014 in Patent Interference No. 105,995.
Pastorio Opposition 1, filed Oct. 31, 2014 in Patent Interference No. 105,995.
Levin Opposition 3, filed Oct. 31, 2014 in Patent Interference No. 105,995.
Pastorio Reply 2, filed Dec. 19, 2014 in Patent Interference No. 105,995.
Levin Reply 1, filed Dec. 19, 2014 in Patent Interference No. 105,995.
Pastorio et al., "Inter Parties Review Certificate" U.S. Pat. No. 8,304,559, Apr. 29, 2019, 2 pages.
International Search Report and Written Opinion for PCT/IB2011/052304, mailed Sep. 26, 2011; ISA/EP.

METHOD FOR THE SYNTHESIS OF 5-AMINO-1-PHENYL-3-CYANO-4-TRIFLUOROMETHYL SULFINYL

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

This application is a 371 U.S. National Stage of International Application No. PCT/IB2011/052304, filed May 26, 2011, and claims priority to Italian patent application No. BS2010A000118, filed Jul. 7, 2010, the disclosures of which are herein incorporated by reference in their entirety.

FIELD OF INVENTION

The present invention relates to a method for the synthesis of 5-amino-1-phenyl-3-cyano-4-trifluoromethyl sulfinyl pyrazole having the following general formula (I), particularly preferred for the synthesis of Fipronil.

BACKGROUND OF INVENTION

The synthesis reaction of the compound having the general formula (I):

(I)

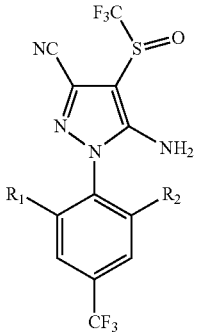

through oxidation of a compound having the general formula (II) has been described in a variety of documents:

(II)

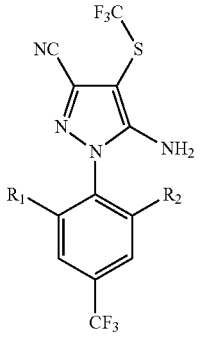

For example, patent EP 0295117 B1 shows a synthesis method using a 3-chlorobenzoic derivative.

Such synthesis method has evident disadvantages both in terms of yield and of costs, the latter related to the impossibility of re-using the oxidising agent.

A method alternative to the previous one was proposed in document WO 01/030760 A1, where the oxidation step is conducted in the presence of trifluoroperacetic acid (TFPA), obtained from trifluoroacetic acid (TFA) in the presence of hydrogen peroxide and boric acid.

However, also this method is unsatisfactory given the following drawbacks: first of all the trifluoroacetic acid is an extremely expensive reagent which, as a consequence, negatively affects the sales price of the product therewith obtained.

Moreover, during the reaction, hydrogen fluoride is released which eats into the vitreous coatings used in industrial reactors despite operating at temperatures close to ambient temperature. To this purpose, document WO 01/030760 A1 suggests using a corrosion inhibitor which nonetheless entails an additional expense to the overall cost of the process.

Moreover, the use of a corrosion inhibitor would not be adequate to protect all the equipment needed for the recovery process of TFA from the corrosive effect of hydrogen fluoride. The TFA recovery and subsequent reutilisation is a necessary operation dictated by the high cost of TFA compared to common oxidants.

The drawbacks of WO 01/030760 A1 have been overcome thanks to the teaching of document WO 2007/122440 A1 where, instead of TFPA, oxidation is conducted in the presence of trichloroperacetic acid (TCPA).

According to the description, TCPA is the effective oxidising species and is formed in situ by the reaction of an oxidising agent with trichloroacetic acid (TCA).

As well as acting as an oxygen acceptor, TCA should also conveniently act as a reaction solvent.

However, at the temperature at which the reaction takes place, TCA is solid (melting point—54-58° C.) so that, for its use as a reaction solvent, a second solvent needs to be added to the TCA to lower its melting point to a temperature compatible with the reaction temperature.

The solvents suitable for this purpose are, among others, dichloroacetic (DCA) and monochloroacetic (MCA) acids.

In particular, a mixture composed of TCA (70-80%) and DCA (30-20%), characterised by a melting point of 15° C.-30° C., has been shown as suitable for conducting such oxidation reaction where, as mentioned above, the sole purpose of the DCA is to depress TCA's melting point.

However, also this method has the drawback that the oxidant species TCA only allows to operate in a temperature range such as to favour the formation of a by-product having the general formula (III), described below, which has a two-fold disadvantage.

First of all, the reaction forming the by-product consumes useful product to the detriment of the yield.

In addition, the by-product having the general formula (III) is difficult to be separated from the compound having the general formula (I) given its low solubility in common organic solvents thereby requiring an expensive purification process adding to the cost.

A further disadvantageous aspect is that the oxidant species TCA can only be used at temperatures compatible with the oxidation reaction of the compound having the general formula (II) to the compound having the general formula (I) if the reaction is conducted in the presence of a species acting as a solvent both for the reagent having the general formula (II) and for the oxidant TCA itself, making both the recovery operation of the product having the general formula (I) and the recovery of the oxidant TCA more complicated.

In addition, it is realistic to believe that, in the teaching of the prior art document WO 2007/122440 A1, the dichloroacetic acid does not transform into dichloroperacetic acid by means of the hydrogen peroxide or other oxidant, because the species TCA, present in significant molar excess of the oxidant and more reactive towards the oxidants, captures all the available oxygen.

The present invention therefore sets out to provide a new method for the preparation of the compound having the general formula (I) using an economically advantageous oxidation method convenient to implement in industrial applications.

SUMMARY OF INVENTION

The present invention relates to a method for the preparation of the 5-amino-1-phenyl-3-cyano-4-trifluoromethyl sulfinyl pyrazole having the described general formula (I), particularly preferred for the synthesis of Fipronil, through oxidation of a compound having the general formula (II) as follows:

(II)

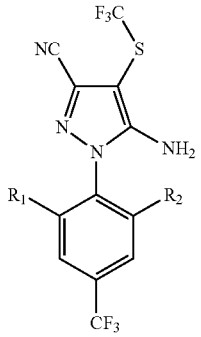

wherein $R_1$ and $R_2$ are independently hydrogen or halogen, and wherein the oxidising agent can be dichloroperacetic acid.

DETAILED DESCRIPTION

The above objective is achieved by a method for the preparation of the compound having the following general formula (I):

(I)

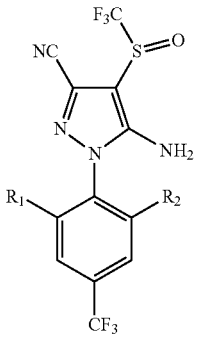

wherein $R_1$ and $R_2$ are independently hydrogen or halogen; through oxidation of a compound having the general formula (II) in the presence of dichloroacetic acid and of an oxidising agent:

(II)

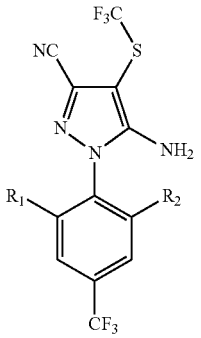

wherein $R_1$ and $R_2$ are defined as above.

As a result, innovatively, the chemical species causing oxidation of the compound having the general formula (II) to a compound having the general formula (I) is preferably dichloroperacetic acid, formed by oxidation of DCA acid through the oxidising agent.

The use of dichloroperacetic acid as an oxidant has never been described in literature. Surprisingly it was found that DCA, in the presence of an oxidant species such as hydrogen peroxide, peroxide or similar, is also itself transformed at low temperatures into the corresponding dichloroperacetic acid and that this species is an excellent oxidant of the compound having the general formula (II).

In other words, the aforesaid oxidation is conducted in the absence of trichloroacetic and/or trichloroperacetic acid, so that the process of the present invention does not require prior solubilisation of the oxidant.

Preferably, $R_1$ and $R_2$ are chlorine or bromine.

Even more preferably, the compound having the general formula (I) is 5-amino-1-(2,6-dichloro-4-trifluoromethylphenyl)-4-trifluorometansulfinyl-1H-pyrazole-3-carbonitril, commercially known by the name of Fipronil (CAS Registry No. 120068-37-3).

Preferably, the production of the dichloroperacetic acid used in the oxidation of the compound having the general formula (II) is performed in situ, by means of the reaction with the oxidising agent.

As a result, according to such variation, the dichloroacetic acid (DCA) performs, after its partial oxidation in dichloroperacetic acid, the dual function of transferring oxygen to the compound having the general formula (II), and acting as a reaction solvent inasmuch as already liquid at the reaction conditions.

The oxidation of the compound having the general formula (II) to a compound having the general formula (I) is a critical operation, in that the reagent used must be sufficiently energetic to quantitatively conduct such reaction, but without generating the (by-)product of subsequent oxidation having the general formula (III):

(III)

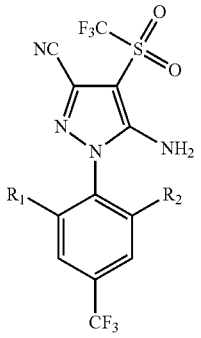

wherein $R_1$ and $R_2$ are again defined as above.

Dichloroperacetic acid proves to be an excellent oxidant for conducting the reaction with good yields and selectivity towards the compound having the general formula (I), without however producing excessive quantities of the undesired product having the general formula (III).

Such good selectivity is not just the result of the intrinsic features of the oxidant species dichloroperacetic acid, but also of the fact that such acid, being liquid, allows to conduct the reaction at a temperature lower than the methods of the prior art, without the use of solvents or melting point depressants.

The present invention therefore allows to operate in the absence of solvents at the same temperatures and to achieve excellent selectivity similar to the ones achieved with trifluoroperacetic acid but without having to use an extremely expensive solvent such as TFA and without having to add corrosion inhibitors which limit, without eliminating, the problem of corrosion of the enamels caused by the hydrogen fluoride generated by such solvent.

According to the present invention, the oxidising agent used is selected from the group comprising benzoyl peroxides, sodium peroxides, t-butyl peroxides and/or hydrogen peroxides.

Among the mentioned oxidising agents, the one that is particularly preferred to oxidise dichloroacetic acid is hydrogen peroxide, in that it can be used in the form of a concentrated aqueous solution.

For example, the concentration of the aqueous solution of hydrogen peroxide is 50%-70% depending on commercial availability, but different concentrations may be just as acceptable.

As regards the precautions suitable for limiting formation of compounds having the aforesaid general formula (III), also the quantity of oxidising agent is a critical variable.

According to an advantageous embodiment, for each mole of compound having the general formula (I),1.0-5.0 moles of oxidising agent are used, preferably 1.1-2.0 equivalents of such agent, more appropriately 1.5 equivalents for each mole.

In addition, advantageously, for each mole of compound having the general formula (II), 1.5 kg-5 kg of dichloroacetic acid are used.

According to a preferred embodiment variation, the temperature at which oxidation takes place is between 0° C. and 35° C.

Preferably, oxidation takes place at a temperature below 20° C., advantageously at a temperature of 0° C.-15° C., more appropriately at about 5° C.

In fact, as mentioned at the beginning, synthesis methods of the prior art do not enable operation at sufficiently low temperatures to limit the formation of the peroxidation product having the general formula (III), which is generated starting from temperatures near 20° C., in excessive quantities even at low conversion values of the product having the general formula (II).

According to the present invention it is preferable, acting on the reaction time or on the quantity of oxidising agent, to conduct the oxidation reaction up to a conversion level of the compound having the general formula (II) of 80%-98%, preferably 90%-95%.

This way, advantageously, the residual quantity of by-product having the general formula (III) is significantly reduced, and a further, complicated final purification of the product having the general formula (I), entailing inevitable losses in terms of yield and resulting waste production, is made substantially superfluous.

According to one embodiment, the method of the present invention further comprises a step of recovering the non-oxidised compound having the general formula (II).

Preferably, the step of recovering comprises a step of dissolving and subsequently recrystallising the compound having the general formula (I) with one or more of the solvents selected from the group comprising toluene, xylenes, chlorobenzene, chlorinated aliphatic solvents and isopropanol.

According to this embodiment, the unconverted compound having the general formula (II), as a result of its greater solubility than the oxidised forms of formulas (I) and (III) in some organic solvents, can be easily removed by means of a solvent and recovered for re-utilisation as a reagent. This way, during the oxidation process the product loss and the waste production is reduced to a minimum, becoming absolutely negligible.

According to a particularly advantageous embodiment, the oxidation of the compound having the general formula (II) occurs in the presence of an acid catalyst, advantageously homogenous.

This embodiment has proven particularly advantageous, especially in virtue of the large volumes involved in the reaction, to achieve reasonable productivity of the plants.

In fact, the aforesaid oxidation reaction of the compound of general formula (II) is conducted for relatively long periods, with large quantities of solvent to avoid the precipitation of the compounds having the general formula (II) and/or general formula (I), and furthermore at relatively low temperatures, such as below 20° C.

Surprisingly it has been noted that the addition of small quantities of an acid catalyst, in particular sulphuric acid, greatly accelerates the oxidation reaction without any negative effect on selectivity, which in any case remains extremely high.

Preferably, the acid catalyst is a strong mineral acid, advantageously chosen from the group consisting in sulphuric acid, methansulphonic acid, hydrochloric acid, nitric acid and their mixtures.

According to an embodiment, the ratio in moles of the compound having the general formula (II) and the acid catalyst is between 0.3 and 1.5, appropriately between 0.5 and 0.9 and, advantageously, is substantially equal to 0.7.

The purpose of the present invention will now be illustrated on the basis of several, non-limiting examples.

EXAMPLE 1

Synthesis of Fipronil

In a glass reactor, 421 grams (1.0 moles) of 5-amino-1-(2,6-dichloro-4-trifluoromethyl-phenyl)-4-trifluorometan-sulfanil-1H-1-pyrazole-3-carbonitrile hereafter "sulphide") are dissolved in 2300 grams of dichloroacetic acid (DCA). The solution obtained is stirred and kept at 20° C. after which 102 grams of hydrogen peroxide in an aqueous solution 50% w/w (1.5 moles) are added.

The reaction is monitored using HPLC analysis until it reaches a conversion level of more than 95% of the reagent sulphide, after which the reaction mixture is diluted with 4 liters of water until the product has precipitated entirely.

The solid thus obtained is filtered, washed with water and dried to obtain 420 grams of product with a purity of 93.5%.

EXAMPLE 2

Synthesis of Fipronil with Subsequent Recovery of Unconverted Reagent Compound Having the General Formula (II)

In a glass reactor 421 grams (1.0 mole) of 5-amino-1-(2, 6-dichloro-4-trifluoromethyl-phenyl)-4-trifluorometan-sulfanil-1H-pyrazole-3-carbonitrile (hereafter "sulphide") are dissolved in 2300 grams of dichloroacetic acid (DCA). The solution obtained is stirred and kept at 20° C., after which 102 grams of hydrogen peroxide in an aqueous solution 50% w/w (1.5 moles) are added.

The reaction is monitored using HPLC analysis until it reaches a conversion level of 92% of the reagent sulphide, so as to limit the formation of the by-product (III) difficult to remove by means of re-crystallisation. When the desired conversion level has been reached the reaction mixture is diluted with 4 liters of water until the product has precipitated entirely.

The solid thus obtained is filtered, washed with water and dried.

After drying the raw product is dissolved while hot in chlorobenzene solvent and re-crystallised by cooling to a low temperature. The solid thus obtained is composed of Fipronil with a purity of over 95%.

The filtrate, containing only sulphide and small quantities of Fipronil, is deprived of the solvent chlorobenzene and added as a reagent to a subsequent oxidation reaction.

EXAMPLE 3

Synthesis of Fipronil with Addition of Sulphuric Acid and Comparison With Example 1 and with WO 2007/122440 A1

In a glass reactor 421 grams (1.0 mole) of 5-amino-1-(2, 6-dichloro-4-trifluoromethyl-phenyl)-4-trifluorometan-sulfanil-1H-pyrazole-3-carbonitrile (hereafter "sulphide") are dissolved in 2300 grams of dichloroacetic acid (DCA). The solution obtained is stirred and kept at 20° C. and subsequently 102 grams of hydrogen peroxide in aqueous solution 50% w/w (1.5 moles) and 70 grams (0.7 moles) of $H_2SO_4$ are added.

The reaction is conducted at a temperature of 5 to 10° C. and monitored by means of HPLC analysis until it reaches a conversion level of over 95% of the reagent sulphide, after which the reaction mixture is diluted with 4 liters of water until the product has precipitated entirely.

The solid thus obtained is filtered, washed with water and dried to obtain 420 grams of a product with a titre of 93.5%.

According to this example, the desired conversion level is reached in about 3 hours compared to the 20 hours of the previous example 1. The reaction conducted at 20° C. according to the examples shown in the earlier document WO 2007/122440 A1, mentioned at the beginning, lasts about 8 hours.

Innovatively, the method of the present invention is conducted in the presence of an oxidising agent and of dichloroacetic acid making a plurality of operations superfluous, for example dissolution, otherwise essential in the known methods.

Advantageously, the method of the present invention allows to achieve higher yields compared to the methods of the prior art, in that the reaction takes place with improved selectivity thereby preventing the consumption of useful product in parasite reactions.

Advantageously, the method of the present invention, once the excess of unconverted reagent (II) has been easily recovered, makes subsequent purification of the compound having the general formula (I) superfluous, which as well as being burdensome in itself is economically disadvantageous.

Advantageously, the use of the oxidising agent of the present invention does not require the use of solvents for the reaction, making the entire process much simpler and economically advantageous in industrial applications.

In fact, according to a further advantageous aspect, the cost of such oxidant is lower than the cost of the oxidants traditionally used.

Advantageously, the function performed by the DCA in the method of the present invention enables economies in terms of costs of the reagents, and simplification of the plant for implementing the teaching.

Advantageously, the process of the present invention makes the use of corrosion inhibitors superfluous and allows to drastically increase the useful life of the equipment used.

It was, in fact, observation of the premature corrosion of the plants which urged the authors of the present invention to look for an oxidant agent alternative to the oxidants traditionally used.

As a result, the aforesaid advantage is twofold in that it derives both from the non-use of a corrosion inhibitor and from the increased useful life of the equipment.

Advantageously, the addition of an acid catalyst makes it possible to considerably reduce reaction times while maintaining a high degree of selectivity of oxidation of the compound having the general formula (II).

Even if not previously specified, a person skilled in the art may, using the expertise typical of the sector, vary or replace some of the aspects described above with other technically equivalent ones.

For example, dichloroperacetic acid may be prepared separately from the place where oxidation of the compound having the general formula (II) takes place, for subsequent addition to the latter.

Moreover, one embodiment envisages that the peroxides illustrated earlier may be replaced or used in conjunction with a peracid and/or a persulphate.

These variations or replacements also fall within the scope of protection defined by the following claims.

In addition, any alternative shown in relation to a particular embodiment may be realised independently of the other variations described.

The invention claimed is:

~~[1. A method for the preparation of the compound having the following general formula (I):~~

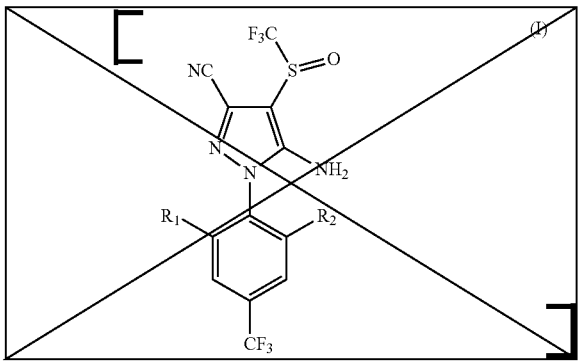

~~wherein $R_1$ and $R_2$ are independently hydrogen or halogen; through oxidation of a compound having the general formula (II) in the presence of dichloroacetic acid and of an oxidising agent:~~

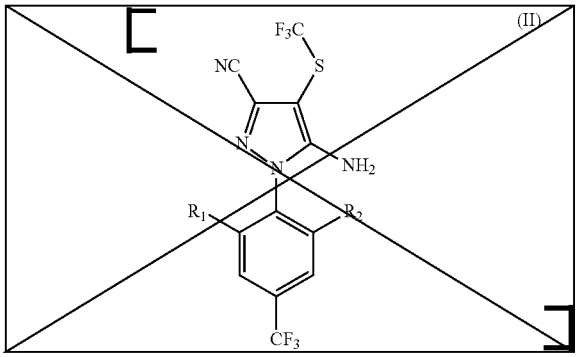

~~wherein $R_1$ and $R_2$ are defined as above, where the oxidising agent is selected from the group comprising benzoyl peroxides, sodium peroxides, t-butyl peroxides and/or hydrogen peroxide, and wherein the oxidation is conducted in the absence of trichloroacetic and/or trichloroperacetic acid.]~~

~~[2. The method according to claim 1, wherein $R_1$ and $R_2$ are chlorine or bromine.]~~

~~[3. The method according to claim 1, wherein the compound having the general formula (I) is 5-amino-1-(2,6-dichloro-4-trifluoromethyl-phenyl)-4-trifluorometansulfinyl-1H-pyrazole-3-carbonitrile.]~~

~~[4. The method according to claim 1, wherein the dichloroacetic acid is oxidised to dichloroperacetic acid through the oxidising agent.]~~

~~[5. The method according to claim 4, wherein oxidation of the dichloroacetic acid takes place in situ.]~~

~~[6. The method according to claim 1, wherein, for each mole of compound having the general formula (I), 1.0-5.0 moles of oxidising agent are used.]~~

~~[7. The method according to claim 1, wherein, for each mole of compound having the general formula (I), 1.1-2.0 equivalents of oxidising agent are used.]~~

~~[8. The method according to claim 1, wherein, for each mole of compound having the general formula (II), 1.5 kg to 5 kg of dichloroacetic acid are used.]~~

~~[9. The method according to claim 1, wherein the temperature at which oxidation takes place is between 0° C. and 35° C.]~~

~~[10. The method according claim 1, wherein the temperature at which oxidation takes place is between 0° C. 20° C. and, preferably is 5° C.]~~

~~[11. The method according to claim 1, further comprising a step of recovering the non-oxidised compound having the general formula (II).]~~

~~[12. The method according to claim 11, wherein the step of recovering comprises a step of dissolving and subsequently recrystallising the compound having the general formula (I) with one or more of the solvents selected from the group comprising toluene, xylene, chlorobenzene, chlorinated aliphatic solvents and isopropanol.]~~

~~[13. The method according to claim 1, wherein the oxidation of the compound having the general formula (II) occurs in the presence of an acid catalyst.]~~

~~[14. The method according to claim 13, wherein the acid catalyst is a strong mineral acid selected from the group consisting in sulphuric acid, methanesulphonic acid, hydrochloric acid, nitric acid and their mixtures.]~~

~~[15. The method according to claim 13, wherein the ratio in moles between the compound of general formula (II) and the acid catalyst is 0.3 to 1.5, and is preferably substantially equal to 0.7.]~~

*16. A method for the preparation of the compound having the following general formula (I):*

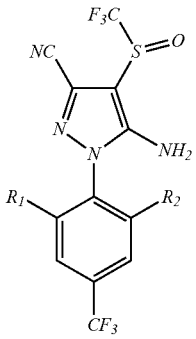

*wherein $R_1$ and $R_2$ are independently hydrogen or halogen;*

*through oxidation of a compound having the general formula (II) in a reaction mixture of dichloroacetic acid and hydrogen peroxide:*

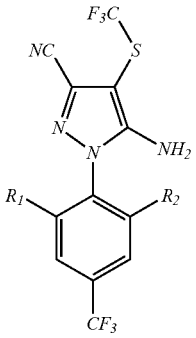

*wherein $R_1$ and $R_2$ are defined as above, and*

*wherein the oxidation is conducted in the absence of trichloroacetic and trichloroperacetic acid, and*

*wherein dichloroacetic acid is oxidized to dichloroperacetic acid in situ through the hydrogen peroxide, and*

*dichloroperacetic acid oxidizes the compound of general formula (II) to the compound of general formula (I).*

*17. The method according to claim 16, wherein $R_1$ and $R_2$ are chlorine or bromine.*

*18. The method according to claim 16, wherein the compound having the general formula (I) is 5-amino-1-[2, 6-dichloro-4-(trifluoromethyl)phenyl]-4-(trifluoromethylsulfinyl)pyrazole-3-carbonitrile.*

*19. The method according to claim 16, wherein the temperature at which oxidation takes place is between 0° C. and 35° C.*

*20. The method according to claim 16, wherein the temperature at which oxidation takes place is between 0° C. and 20° C.*

*21. The method according to claim 16, wherein the temperature at which the oxidation takes place is about 5° C.*

*22. The method according to claim 16, wherein, for each mole of compound having the general formula (I), 1.0-5.0 moles of hydrogen peroxide are used.*

*23. The method according to claim 16, wherein, for each mole of compound having the general formula (I), 1.1-2.0 equivalents of hydrogen peroxide are used.*

*24. The method according to claim 16, wherein, for each mole of compound having the general formula (II), 1.5-5 kg of dichloroacetic acid are used.*

*25. The method according to claim 16, wherein, the oxidation is conducted at a temperature between 0° C. and 20° C., for each mole of compound having the general formula (I), 1.0-5.0 moles of hydrogen peroxide and 1.5-5 kg of dichloroacetic acid are used.*

*26. The method according to claim 16, wherein, 80%-98% of the compound having the general formula (II) is converted to the compound having the general formula (I).*

* * * * *